(12) United States Patent
Kim et al.

(10) Patent No.: US 9,295,667 B2
(45) Date of Patent: Mar. 29, 2016

(54) PHARMACEUTICAL COMPOSITION FOR PREVENTING OR TREATING DIABETES OR FATTY LIVER CONTAINING A CYP4A INHIBITOR AS AN ACTIVE INGREDIENT

(71) Applicant: Korea Basic Science Institute, Daejeon (KR)

(72) Inventors: Gun-Hwa Kim, Daejeon (KR); Soohyun Kim, Daejeon (KR); Jong-Soon Choi, Daejeon (KR); Seung Il Kim, Daejeon (KR); Edmond Changkyun Park, Daejeon (KR)

(73) Assignee: Korea Basic Science Institute, Daejeon (KR)

( * ) Notice: Subject to any disclaimer, the term of this patent is extended or adjusted under 35 U.S.C. 154(b) by 0 days.

(21) Appl. No.: 14/178,090

(22) Filed: Feb. 11, 2014

(65) Prior Publication Data
US 2014/0275198 A1    Sep. 18, 2014

Related U.S. Application Data

(63) Continuation of application No. PCT/KR2012/006395, filed on Aug. 10, 2012.

(30) Foreign Application Priority Data

Aug. 11, 2011    (KR) .................. 10-2011-0080208

(51) Int. Cl.
| | | |
|---|---|---|
| *A61K 31/41* | (2006.01) | |
| *A61K 31/415* | (2006.01) | |
| *A61K 31/20* | (2006.01) | |
| *A61K 31/18* | (2006.01) | |
| *A61K 31/15* | (2006.01) | |
| *A61K 31/4192* | (2006.01) | |
| *A61K 31/155* | (2006.01) | |
| *A61K 31/201* | (2006.01) | |
| *A61K 31/4174* | (2006.01) | |

(52) U.S. Cl.
CPC .............. *A61K 31/4192* (2013.01); *A61K 31/15* (2013.01); *A61K 31/155* (2013.01); *A61K 31/18* (2013.01); *A61K 31/201* (2013.01); *A61K 31/4174* (2013.01)

(58) Field of Classification Search
CPC ..... A61K 31/15; A61K 31/155; A61K 31/18; A61K 31/201; A61K 31/4174; A61K 31/4192
USPC ......................... 514/359, 399, 560, 601, 640
See application file for complete search history.

(56) References Cited

U.S. PATENT DOCUMENTS

2005/0124618 A1*  6/2005  Roman et al. .......... A61K 31/00
                                                    514/237.5

FOREIGN PATENT DOCUMENTS

WO    WO 0236108 A2 *   5/2002    ............. A61K 31/15

OTHER PUBLICATIONS

Sato et al., "Discovery of a N'-Hydroxyphenylformamidine Derivative HET0016 as a Potent and Selective 20-HETE Synthase Inhibitor", 2001, Bioorg. Med. Chem. Lett., 11(23), pp. 2993-2995.*

* cited by examiner

*Primary Examiner* — My-Chau T Tran
(74) *Attorney, Agent, or Firm* — Mintz Levin Cohn Ferris Glovsky and Popeo, P.C.; Kongsik Kim; Richard B. Emmons

(57) ABSTRACT

The present invention relates to a pharmaceutical composition for preventing or treating diabetes or fatty liver, and more specifically relates to a pharmaceutical composition for preventing or treating diabetes or fatty liver containing a CYP4A (cytochrome P450A) inhibitor as an active ingredient. According to the present invention, the CYP4A inhibitor suppresses endoplasmic reticulum stress, reduces the blood insulin concentration and suppresses apoptosis of liver cells, and hence exhibits effects in preventing or treating diabetes or fatty liver.

7 Claims, 22 Drawing Sheets

HET0016

PHARMACEUTICAL COMPOSITION FOR PREVENTING OR TREATING DIABETES OR FATTY LIVER CONTAINING A CYP4A INHIBITOR AS AN ACTIVE INGREDIENT

CROSS REFERENCE TO RELATED APPLICATION

This is a continuation of International Application No. PCT/KR2012/006395 filed on Aug. 10, 2012, which claims priority to Korean Application No. 10-2011-0080208 filed on Aug. 11, 2011, which applications are incorporated herein by reference.

TECHNICAL FIELD

The present invention relates to a pharmaceutical composition for preventing or treating diabetes or fatty liver. More particularly, the present invention relates to a pharmaceutical composition for preventing or treating diabetes or fatty liver comprising a CYP4A (cytochrome P450 4A) inhibitor as an active ingredient.

BACKGROUND ART

Type 2 diabetes mellitus (T2DM) is one of the most prevalent and serious metabolic disease characterized by an elevated level of blood glucose, affecting 6.4% of the world population and accounting for greater than 90% of diabetic patients.

Meanwhile, obesity is a major underlying pathology for the development of T2DM, non-alchoholic steatohepatitis (NASH) and cardiovascular disease. While insulin resistance is condition in which cells fail to utilize insulin properly, obesity is a central risk factor for the development of insulin resistance in the muscles, the fatty tissues and the liver of those having T2DM.

While an underlying mechanism for insulin resistance is still unclear, endoplasmic reticulum (ER) stress has been suggested as a new mechanism for the development of insulin resistance in obese individuals. ER stress can be caused by the disruption of $Ca^{+2}$ homeostasis, overload of protein/lipid biosynthesis and oxidative stress, which then trigger an evolutionarily conserved mechanism referred to as the unfolded protein response (UPR) pathway including IRE1, ATF6 and PERK. Recently, it has been shown that ER stress and UPR pathway play a role in the pathogenesis of diabetes. However, the precise mechanism directly regulating the UPR pathway in diabetes is poorly understood.

In a mammalian liver, the members of the cytochrome P450 enzyme family (CYP450s) act mainly as ER membrane-localized NADPH monooxygenases responsible for catalyzing the oxidative metabolism of a wide variety of foreign chemicals and endogenous compounds. Under the conditions of obesity and diabetes, it has been reported that the expression profiles of CYP450s in the liver tissues are dynamic. In particular, CYP2E1 has been found to decrease the expression of ER chaperone proteins and induce ER protein damage and stress via its catalytic activation of pro-oxidants.

SUMMARY

Therefore, CYP450s, which are novel substances responsible for regulating UPR signaling and insulin resistance in the liver, may be related to the development of ER stress and T2DM.

The object of the present invention is to determine whether the regulation of the expression of CYP4A (cytochrome P450 4A) among the ER stress-related members of the cytochrome P450 enzyme family (CYP450s) is effective for the prevention or treatment of diabetes or fatty liver, leading to the provision of a CYP4A (cytochrome P450 4A) inhibitor in a pharmaceutical composition for preventing or treating diabetes or fatty liver.

In order to achieve the object of the present invention, the present invention provides a pharmaceutical composition for preventing or treating diabetes or fatty liver disease comprising a CYP4A (cytochrome P450 4A) inhibitor as an active ingredient.

The CYP4A (cytochrome P450 4A) inhibitor according to the present invention includes N-hydroxy-N'-(4-butyl-2-methylphenyl)-formamidine or derivatives thereof.

The diabetes according to the present invention includes Type 2 diabetes mellitus (T2DM).

The diabetes according to the present invention may be induced by obesity.

The CYP4A inhibitor according to the present invention decreases ER stress.

The CYP4A inhibitor according to the present invention inhibits the level of blood insulin.

The CYP4A inhibitor according to the present invention inhibits the apoptosis of hepatocytes.

BRIEF DESCRIPTION OF DRAWINGS

FIG. 8 shows the result of the enzymatic activity assay of Cyp4a.

DETAILED DESCRIPTION

Figure 1:
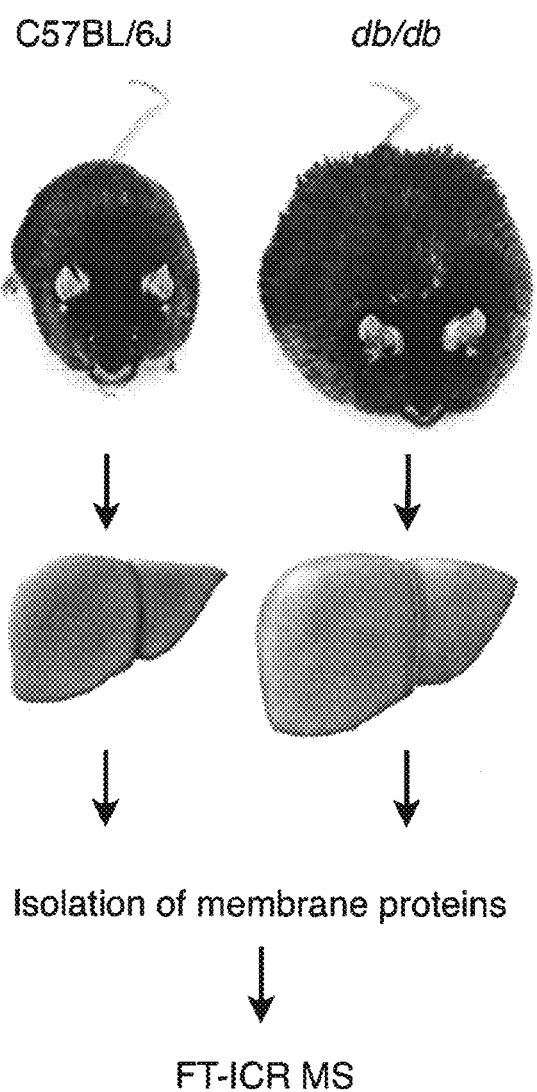
FIG. 1 is a diagram illustrating a procedure in which membrane proteins are isolated from the liver tissues of ten (10)-week-old C57BL/6J control and db/db mice and identified by Fourier Transform Ion Cyclotron Resonance (FT-ICR) mass spectrometry.

While determining that the inhibition of CYP4A (cytochrome P450 4A) can be a potent target for treating ER stress-induced insulin resistance and apoptosis, the inventors of the present application suggest that an CYP4A inhibitor according to the present invention may be utilized in a pharmaceutical composition for preventing or treating obesity-related diabetes or fatty liver.

In particular, since endoplasmic reticulum (ER) stress has been known to be implicated in the development of diabetes, it is very important in the present invention to understand the basic mechanism for regulating ER stress. Hence, while analyzing the biochemical and physiochemical properties of CYP4A (cytochrome P450 4A) using a specific CYP4A inhibitor, N-hydroxy-N'-(4-butyl-2-methylphenyl)-formamidine (HET0016) or derivatives thereof as described in the detailed description of the present application, the inventors have sought to determine the importance of CYP4A in the improvement of diabetes and ER stress-induced liver insulin resistance & apoptosis. The discovery by the inventors suggests that decrease in CYP4A activity may become a potent target for treating diabetes or fatty liver.

Therefore, the present invention provides a pharmaceutical composition for preventing or treating diabetes or fatty liver comprising a CYP4A (cytochrome P450 4A) inhibitor as an active ingredient.

CYP (cytochrome P450) proteins are enzymes which mediate NADPH-dependent electron transport and oxidize various substances such as steroids, fatty acids and xenobiotics. Particularly, CYP4A is expressed in the liver and the kidneys and located on the membranes of endoplasmic reticulum (ER) in which it plays an important role in the metabolism of various fatty acids. CYP includes various alternative splicing varients possessing the same function. CYP4A according to the present invention may be Human Cyp4a11 (GI:158937241, NP_000769), Human Cyp4a22 (GI: 62952505, NP_001010969), Mouse Cyp4a10 (GI: 227116293, NP_034141), Mouse Cyp4a12a (GI:86198311, NP_803125), Mouse Cyp4a12b (GI:86198313, NP_758510) or Mouse Cyp4a14 (GI:164518936, NP_031848). Preferably, CYP4A according to the present invention may be Human Cyp4a11 (GI:158937241, NP_000769; SEQ ID NO:1) or Human Cyp4a22 (GI:62952505, NP_001010969; SEQ ID NO: 2).

```
                                                SEQ ID NO: 1
MSVSVLSPSRLLGDVSGILQAASLLILLLLLIKAVQLYLHRQWLLKALQ

QFPCPPSHWLFGHIQELQQDQELQRIQKWVETFPSACPHWLWGGKVRVQ

LYDPDYMKVILGRSDPKSHGSYRFLAPWIGYGLLLLNGQTWFQHRRMLT

PAFHYDILKPYVGLMADSVRVMLDKWEELLGQDSPLEVFQHVSLMTLDT

IMKVAFSHQGSIQVDRNSQSYIQAISDLNNLVFSRVRNAFHQNDTIYSL

TSAGRWTHRACQLAHQHTDQVIQLRKAQLQKEGELEKIKRKRHLDFLDI

LLLAKMENGSILSDKDLRAEVDTFMFEGHDTTASGISWILYALATHPKH

QERCREEIHSLLGDGASITWNHLDQMPYTTMCIKEALRLYPPVPGIGRE

LSTPVTFPDGRSLPKGIMVLLSIYGLHHNPKVWPNPEVFDPFRFAPGSA

QHSHAFLPFSGGSRNCIGKQFAMNELKVATALTLLRFELLPDPTRIPIP

IARLVLKSKNGIHLRLRRLPNPCEDKDQL
                                                SEQ ID NO: 2
MSVSVLSPSRRLGGVSGILQVTSLLILLLLLIKAAQLYLHRQWLLKALQ

QFPCPPSHWLFGHIQEFQHDQELQRIQERVKTFPSACPYWIWGGKVRVQ

LYDPDYMKVILGRSDPKSHGSYKFLAPRIGYGLLLLNGQTWFQHRRMLT
```

PAFHNDILKPYVGLMADSVRVMLDKWEELLGQDSPLEVFQHVSLMTLDT

IMKSAFSHQGSIQVDRNSQSYIQAISDLNSLVFCCMRNAFHENDTIYSL

TSAGRWTHRACQLAHQHTDQVIQLRKAQLQKEGELEKIKRKRHLDFLDI

LLLAKMENGSILSDKDLRAEVDTFMFEGHDTTASGISWILYALATHPKH

QERCREEIHGLLGDGASITWNHLDQMPYTTMCIKEALRLYPPVPGIGRE

LSTPVTFPDGRSLPKGIMVLLSIYGLHHNPKVWPNLEVFDPSRFAPGSA

QHSHAFLPFSGGSRNCIGKQFAMNQLKVARALTLLRFELLPDPTRIPIP

MARLVLKSNGIHLRLRRLPNPCEDKDQL

The CYP4A (cytochrome P450 4A) inhibitor according to the present invention refers to any substance inhibiting the enzymatic or physiological function of CYP4A, including chemical compounds, antibodies against CYP4A or other various polypeptides which possess the above mentioned activity.

The above described chemical compounds may be preferably N-hydroxy-N'-(4-butyl-2-methylphenyl)-formamidine, dibromododecenyl methylsulfonimide (DDMS, American Journal of Pathology 2005, 166:615-624), 1-aminobenzotriazole (ABT, Am J Physiol Renal Physiol 2003, 285:F295-F302) or 17-octadecynoic acid (17-ODA, Am J Physiol Heart Circ Physiol 2001, 280:H1840-1845), miconazole (WO2002/036108) or derivatives thereof. The above mentioned derivatives of N-hydroxy-N'-(4-butyl-2-methylphenyl)-formamidine may include publicly known ones of N-hydroxy-N'-(4-butyl-2-methylphenyl)-formamidine (See M. Sato et al., Bioorg. Med. Chem. Lett. 11 (2001) 2993-2995, Table 1).

The derivatives of N-hydroxy-N'-(4-butyl-2-methylphenyl)-formamidine may be ones having the following chemical formulas:

[Chemical Formula 1]

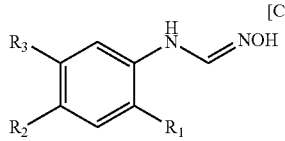

| $R_1$ | $R_2$ | $R_3$ |
|---|---|---|
| Me | Bu | H |
| Me | H | H |
| Me | H | Bu |
| Bu | H | H |
| H | Me | H |
| H | Et | H |
| H | Bu | H |
| H | hexyl | H |
| H | i-Pr | H |
| H | s-Bu | H |
| H | t-Bu | H |
| H | PhCH$_2$ | H |
| H | PrO | H |

[Chemical Formula 2]

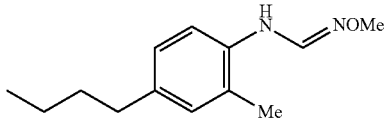

[Chemical Formula 3]

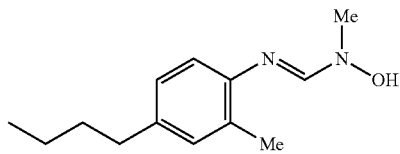

[Chemical Formula 4]

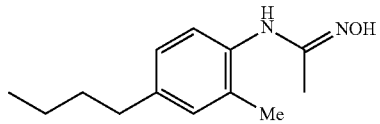

[Chemical Formula 5]

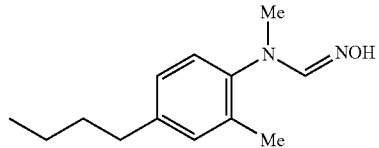

The abbreviations in the above chemical formulas are as follows: Me (methyl), Et (ethyl), i-Pr (isopropyl), Bu (butyl), s-Bu (sec-butyl or secondary butyl), t-Bu (tert-butyl or tertiary butyl), PhCH$_2$ (benzyl), and PrO (propoxy).

Meanwhile, the CYP4A (cytochrome P450 4A) inhibitor according to the present invention may refer to a substance which inhibits the synthesis of CYP4A, as well as one which inhibits the enzymatic activity of CYP4A. While the synthesis of CYP4A refers to the expression of CYP4A in cells via, for instance, its gene expression, the substance inhibiting the synthesis of CYP4A may be antisense RNA or siRNA (small interference RNA) against Cyp4a gene.

CYP4A (cytochrome P450 4A) inhibitor according to the present invention may be effectively utilized for preventing or treating diabetes or fatty liver.

Diabetes is one of metabolic disorders which is related to deficiency of insulin and caused by genetic or acquired factors such as obesity, infection and pregnancy. Diabetes according to the present invention includes type 2 diabetes mellitus which may be induced by obesity.

Fatty liver is a condition of abnormal accumulation of lipids (especially, triglycerides) in the liver, including alcoholic fatty liver, hyper-nutrition-related fatty liver and diabetic fatty liver.

The CYP4A inhibitor according to the present invention acts as a mechanism for inhibiting ER stress, the level of blood insulin, and the apoptosis of hepatocytes.

Further, the present invention provides a method for treating diabetes or fatty liver, comprising administering to a subject in need thereof an effective amount of CYP4A inhibitor. Still furthermore, the present invention provides use of CYP4A inhibitor for the preparation of an agent for treating diabetes or fatty liver.

As used herein, the term "an effective amount" means an amount of a pharmaceutical composition or formulation according to the present invention which is effective for preventing or treating diabetes or fatty liver. As described herein, the term "a subject" means an animal, preferably a mammal (especially, an animal including a human being), while it may include a cell, a tissue or an organ derived from an animal. Such a subject may include a patient for whom a treatment is needed.

A composition according to the present invention may include a pharmaceutical composition. The pharmaceutical composition according to the present invention may be provided in a suitable formulation which comprises a peptide, a substance or agent, a marker substance or in combination thereof or together with a pharmaceutically acceptable carrier. As used herein, the term "pharmaceutically acceptable" refers to one which is physiologically acceptable and non-toxic, i.e. when administered to a human being, generally causing no allergic reactions (such as gastrointestinal disorder and dizziness) or similar reactions thereto. The pharmaceutically acceptable carrier according to the present invention may include all kinds of solvents, dispersion mediums, oil-in-water or water-in-oil emulsions, aqueous compositions, liposomes, microbeads, microsomes, and biodegradable nanoparticles. Preferably, a composition according to the present invention may comprise 0.001 to 99.999 weight % of the pharmaceutical composition according to the present invention and 99.999 to 0.001 weight % of the pharmaceutically acceptable carrier.

Meanwhile, the pharmaceutical composition according to the present invention may be formulated with a suitable carrier depending on various administration routes. The pharmaceutical composition according to the present invention may be administered orally or parenterally, but not limited thereto. The parenteral administration routes may include various routes such as transdermal, nasal, peritoneal, intramuscular, subcutaneous, and intravenous routes.

For the purpose of oral administration, the pharmaceutical composition according to the present invention may be formulated with a suitable carrier for oral administration in the form of powders, granules, tablets, pills, sugar-coated tablets, capsules, liquids, gels, syrups, suspensions, wafers and so on, by using known methods in the art. Examples of the suitable carrier include sugars such as lactose, dextrose, sucrose, sorbitol, mannitol, xylitol, erythritol, and maltitol; starches such as corn starch, wheat starch, rice starch and potato starch; celluloses such as cellulose, methyl cellulose, sodium carboxymethylcellulose and hydroxypropylmethyl cellulose; fillers such as gelatin and polyvinylpyrrolidone. In addition, a disintegrating agent such as cross-linked polyvinylpyrrolidone, agar, alginic acid and sodium alginate may be added. Furthermore, the pharmaceutical composition according to the present invention may additionally include, but not limited to, anti-aggregating agents, lubricants, wetting agents, flavoring agents, emulsifiers, and preservatives.

In case of parenteral administration, the pharmaceutical composition according to the present invention may be formulated with a suitable carrier for parenteral administration in a form of injectable, transdermal or nasal inhaler preparations, by using known methods in the art. The injectable preparation is required to be sterilized and protected from the contamination of microorganisms such as bacteria and fungi. The suitable carrier for injectable preparations includes, but is not limited to, water, ethanol, polyol (such as glycerol, prophylene glycol, and liquid polyethylene glycol), a combination thereof and/or solvents or dispersing mediums containing vegetable oils. More preferably, the suitable carrier includes isotonic solutions such as Hanks' solution, Ringer's solution, triethanol amine-containing PBS (phosphate buffered saline) or injectable sterilized water, 10% ethanol, 40% prophylene glycol, and 5% dextrose. In order to avoid the contamination of microorganisms, the injectable preparations may additionally contain various antibacterial or antifungal agents such as paraben, chlorobutanol, phenol, sorbic acid, and thimerosal. In general, the injectable preparations may additionally comprise an isotonic agent such as sugar and sodium chloride. The above preparations or formulations are described in the well-known literature in the pharmaceutical chemistry field (See Remington's Pharmaceutical Sciences, 15th Edition, Mack Publishing Company, Easton, Pa., 1975).

For inhaling preparations, the substance according to the present invention may be administered conveniently in the form of aerosol spray from a pressurized pack or a fog generator, by using a suitable propellant such as dichloro fluoro methane, trichloro fluoro methane, dichloro tetrafluoro ethane, carbon dioxide or other suitable gas. For a pressurized aerosol, a dosage unit may be determined by providing a valve to deliver a metered amount. For instance, gelatin capsules and cartridges used for an inhaler or an insufflator may be formulated to contain a powder mixture of a substance and a suitable powder base such as lactose or starch.

Other pharmaceutically acceptable carriers may be considered as listed in the following document (Remington's Pharmaceutical Sciences, 19th ed., Mack Publishing Company, Easton, Pa., 1995).

Further, the pharmaceutical composition according to the present invention may additionally contain one or more buffering agents (e.g. saline and PBS), carbohydrates (e.g. glucose, mannose, sucrose and dextran), stabilizing agents (e.g. sodium hydrogen sulfite, sodium sulfite and ascorbic acid), anti-oxidants, bacteriostatic agents, chelating agents (e.g. EDTA and glutathione), adjuvants (e.g. aluminum hydroxide), suspending agents, thickening agents and/or preservatives (e.g. benzalkonium chloride, methyl- or propyl-paraben, chlorobutanol).

Still further, the pharmaceutical composition according to the present invention may be formulated by using known methods in the art to provide a rapid, sustained or delayed release of the active ingredient upon its administration to a mammal subject.

The pharmaceutical composition formulated by the above described methods may be administered in its effective amount via various routes including oral, transdermal, subcutaneous, intravenous or intramuscular routes. The term "effective amount" as used herein means an amount of a substance or an extract by which, upon the administration of the substance or the extract, its diagnostic or therapeutic effect is detectable. Dosage of the pharmaceutical composition according to the present invention may be suitably determined by considering various factors such as administration route, a subject to be administered, types of disease and disease severity, age, sex, body weight, individual difference, and disease condition. Preferably, while the pharmaceutical composition comprising the peptide according to the present invention may comprise a different amount of the active ingredient depending on the severity of disease, it may be generally administered several times a day in an effective amount of 10 μg to 10 mg per each administration for an adult subject, with a total amount of 0.001 to 100 mg/kg (weight) per day depending on different individuals.

Processing with nucleotides and proteins as described herein may be referred to the following documents (See Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, $2^{nd}$ Ed., Cold Spring Harbor Laboratory Press (1989); Deutscher, M., Guide to Protein Purification Methods Enzymology, Vol. 182. Academic Press. Inc., San Diego, Calif. (1990)).

EXAMPLES

Hereinafter, the present invention will be described in detail by the following examples. It is to be understood, however, that these examples are presented only for illustrative purpose and are not construed to limit the scope of the present invention.

Experimental Methods

1. Animal and Histological Experiments

Male C57BL/6J and C57BL/KsJ-db/db mice were purchased from Japan SLC. HET0016 (5 mg/kg/day) and clofibrate (400 mg/kg/day) were injected intraperitoneally into eight (8)-week-old mice for two (2) weeks. Control littermate mice for HET0016 were treated with DMSO, while control littermate mice for clofibrate were treated with corn oil. Intraperitoneal glucose tolerance test (IPGTT) was performed after overnight fasting followed by intraperitoneal injection of lg/kg of glucose dissolved in PBS. The concentrations of blood glucose were measured using a One Touch Ultra glucometer (LifeScan, Inc.) before (0 min) and at 15, 30, 60, 90 and 120 min. after glucose injection. Livers isolated from 10-week-old mice were fixed in 10% neutral buffered formalin solution (Sigma), and paraffin sections were stained with hematoxylin-eosin.

2. Cell Cultures and Chemical Processing

HepG2 cells were cultured in a Dulbecco's Modified Eagle Medium (DMEM, Gibco) Low Glucose supplemented with heat-inactivated 10% fetal bovine serum (FBS) and antibiotics at 37° C. in the presence of 5% moisturized $CO_2$ and 95% air. The above cells were plated in a concentration of $3\times10^4$ cells/cm$^2$ and maintained in the cell culture medium for 24 hours prior to the following chemical processing. 4 µg/ml of tunicamycin was treated without HET0016 or with 4 µM of HET0016 for six (6) hours. As a control, HepG2 cells were treated with DMSO.

3. Isolation of Membrane Proteins and Mass Spectroscopy

As described above, membrane proteins were isolated from the liver tissues of the C57BL/6J or db/db mice by using sodium carbonate. In brief, the mice livers were homogenized, followed by the dilution of the resulting liver lys ate with 100 mM sodium carbonate of pH 11.5 at 0° C. for 30 minutes. The obtained suspension was centrifuged at 50,000 rpm at 4° C. for 1 hour. The membrane pellets as obtained were washed off with distilled water and subsequently dissolved in SDS-PAGE. For the purpose of mass spectroscopy, 10 µg of protein samples were isolated by means of 12% SDS-PAGE. The Gel was stained with Coomassie Brilliant Blue R-250 and fractionized in six parts according to molecular weight. Reduction and alkylation of cysteines of each protein in each gel part were performed, followed by breaking-down with trypsin (1.2 µg) at 37° C. for 16 hours. The obtained broken-down peptides were extracted with an extracting solution (50mM sodium bicarbonate, 50% acetonitrile and 5% trifluoroacetic acid) and subsequently dissolved in a sample solution containing 0.02% formic acid and 0.5% acetic acid. For the application of mass spectrometry, the above peptide samples were concentrated over trapping column (PROXEON) of Easy-column™ (L 2 cm, ID 100 µm, 120 Å, C18-A1), eluted from the above column, and directed to reverse-phase column (PROXEON) of Easy-column™ (L 10 cm, ID 75 µm, 120 Å, C18-A2) at the flow velocity of 200 nl/min. Then, the peptides were eluted for 120 minutes by a gradient of 0-65% acetonitrile. All the MS and MS/MS spectrums in LTQ-Velos ESI ion trap mass spectrometry (Thermo Scientific) were obtained in a data-dependent mode. Upon scanning total MS (over a range of 300 to 2,000 m/z) followed by dynamic exclusion enablement, MS/MS scanning was conducted three times over the most abundant precursor ions in the MS spectrum. For the purpose of protein identification, MS/MS spectrum was evaluated with MASCOT (Matrix Science). Human genomic sequences were used as a database for protein identification. The mass tolerance of a parent ion or a fragment ion was 0.8 Da. For diverse variation of trypsin-like peptides, carbamidomethylation of cysteines and oxidation of methionines were considered in MS/MS analysis.

4. Preparation of Microsomes from Mice Livers

Liver microsomes were prepared from fresh mice livers by applying a slight modification to the above described methods. Separated livers were thoroughly sprinkled with 1.15% KCl solution. Subsequently, the livers were homogenized with 4 times volume of a homogenizing buffer (0.1 M Tris-HCl, pH 7.4; 0.1 M KCl; mM EDTA, pH 7.5; 25 µM butylated hydroxyltoluene). In order to remove un-destructed cells, nuclei and mitochondria, the obtained homogenate was centrifuged in a low-powered centrifugation (1,000× g, 4° C. for 15 min.) The obtained supernatant was then centrifuged in a higher powered centrifugation (100,000× g, 4° C. for 60 min.), resulting in the precipitation of microsomes. Pellets of compactly packed microsomes were re-suspended in 3 ml of an ice-cooled pyrophosphate buffer (0.1 M potassium pyrophosphate; 1 mM EDTA, pH 7.5; 20 µM butylated hydroxyltoluene) by using a homogenizer, followed by further centrifugation at 100,000× g, 4° C. for 60 min. The washed microsome pellets were finally suspended in 2 ml of an ice-cooled microsome buffer (10 mM Tris-HCl, pH 7.4; 1 mM EDTA, pH 7.5; 20% glycerol).

5. Western Blotting Assay

Proteins were denatured at 95° C., and separated by SDS-PAGE, followed by electroblotting on a membrane made of nitrocellulose (NC) or polyvinylidene difluoride (PVDF). After blocking in TBST (Tris-buffered Saline, 0.1% Tween-20) containing 5% non-fat milk (skim milk) or 5% bovine serum albumin (BSA), the membrane was incubated with labeled primary antibodies. Subsequently, the membrane was washed with TBST and further incubated with secondary antibodies coupled with horseradish peroxides. Protein blots were detected by using ECL kit and visualized by a luminescence imaging analyzer of LAS-4000 mini system and software (FujiFilm). Following antibodies were utilized: mouse anti-β-actin (sc-47778), rabbit anti-CYP4A (sc-98988, Santa Cruz Biotechnology), mouse anti-ATF6 (IMG-273, Imgenex), mouse anti-eIF2α (ab5369), rabbit anti-phospho-eIF2α Ser51 (ab32157), rabbit anti-IRE1 (ab37073, Abcam), rabbit anti-PERK(#3192), rabbit anti-phospho-PERK Thr980 (#3179), rabbit anti-BiP (#3177), mouse anti-CHOP (#2895), rabbit anti-SAPK/JNK (#9252), rabbit anti-phospho-SAPK/JNK Thr813/Tyr185 (#9251), rabbit anti-Insulin receptor β (#3025), rabbit anti-phospho-Insulin receptor β Tyr1150/1151 (#3024), rabbit anti-Akt (#4691), rabbit anti-phospho-Akt Ser473 (#4060), rabbit anti-Bcl-2 (#2876), rabbit anti-Bax (#2772), rabbit anti-divided caspase-3 (#9664), rabbit anti-divided caspase-9 (#9509), rabbit anti-Bax (#2772, Cell Signaling Technology), rabbit anti-ERP72 (obtained from Dr. O. Y. Kwon, College of Medicine, Chungnam National University).

6. Reverse Transcription and Real-time RT PCR

In order to extract total RNAs, mice liver tissues were homogenized with TRI reagent (Molecular Research Center, Inc.) and then centrifuged at 12,000 rpm and 4° C. for 10 minutes. For the purpose of phase separation, the obtained supernatant was vigorously mixed with 0.1 ml of BCP (1-bromo-3-chloropropane; Molecular Research Center, Inc.) per 1 ml of TRI reagent which was used for homogenization. After centrifuging at 12,000 rpm and 4° C. for 10 minutes, water phase was used for further extraction with phenol chloroform. Total RNAs were then precipitated and dissolved in water without RNAse. Reverse transcription of extracted RNAs was conducted with random hexamer primers by using Transcriptor First Strand cDNA Synthesis Kit (Roche). While real time PCR was performed by using Light-Cycler 480 DNA SYBR Green I Master (Roche), Real-Time PCR System (Roche) was used in accordance with the manufacturer's instructions to obtain PCR products. Following primers were utilized: CPY4A10, 5'-AGCCA-CAAGGGCAGTGTTCAGG-3' (forward primer) and 5'-CCAAGCGGCCATTGGAAGAAAG-3' (reverse primer); CPY4Al2, 5'-GCCTTATACGGAAATATGGCA-3' (forward primer) and 5'-TGGAATCCTGGCCAACAATC-3' (reverse primer); CPY4A14, 5'-TGAATTGCTGCCAGATCCCAC-CAGGATC-3' (forward primer) and 5'-GTTCAGTGGCTG-GTCAGA-3' (reverse primer); XBP1, 5'-3' (forward primer) and 5'-3' (reverse primer); and CHOP, 5'-3' (forward primer) and 5'-3 ' (reverse primer).

7. Measurement of Metabolites

While the mice were sacrificed, their blood was obtained with their hearts being punctured. The concentration of serum insulin was determined by using a commercial mouse serum insulin ELISA kit (Shibayagi Co., Ltd.) according to the manufacturer's instructions. Lipid peroxidation was measured by using OxiSelect™ TBARS Assay Kit (Cell Biolabs, Inc.) to quantify malondialdehyde (MDA), a natural by-product of lipid peroxidation in the liver homogenates. The level of triglyceride in the mice livers was measured by using Triglyceride Quantification Kit (Abcam).

8. Analysis of the Enzymatic Activity of CYP4A

The products from the reaction of lauric acid and the liver microsome extracts of the controls and db/db mice were observed in Gas Chromatography/Mass Spectrometry (GC/MS) as follows. 100 µM lauric acid and 0.2 mg of the liver microsome extracts of the controls or db/db mice were incubated in 0.5 ml of 100 mM potassium phosphate buffer (pH 7.4) at 37° C. for 30 minutes, obtaining metabolic products. After the incubation was completed, the obtained metabolic products were extracted by using $CH_2Cl_3$, while organic solvents were removed with the flow of nitrogen. The remaining was dissolved in N,O-bis(trimethylsilyl)-trifluoroacetamide (BSTFA: 50 µl) containing trimethylchlorosilane (1%, v/v). The solution was moved to a glass vial in which it was further incubated at 75° C. for 20 minutes to obtain trimethylsilyl products. Subsequently, the obtained products were subjected to GC/MS analysis over Shimadzu QP2010 (Column:Length: 30 cm, Inner Diameter: 0.25 mm, Film thickness: 0.1 µm) using electron-impact ionization. The temperature of GC oven was programmed at 70° C. for 1 minute initially, being subsequently increased at a following speed: 25° C. /min up to 170° C., 5° C./min up to 200° C. and 20° C./min. up to 280° C. Then, the GC oven was maintained at 280° C. for 5 minutes. Sources and interfaces for MS were maintained at 250° C. and 280° C., respectively, while four (4) minutes' solvent delay was utilized. The above products were identified through their characteristic mass fraction patterns. The distribution of the products was based on the relative peak area of their gas chromatogram.

Experimental Results

Figure 2:
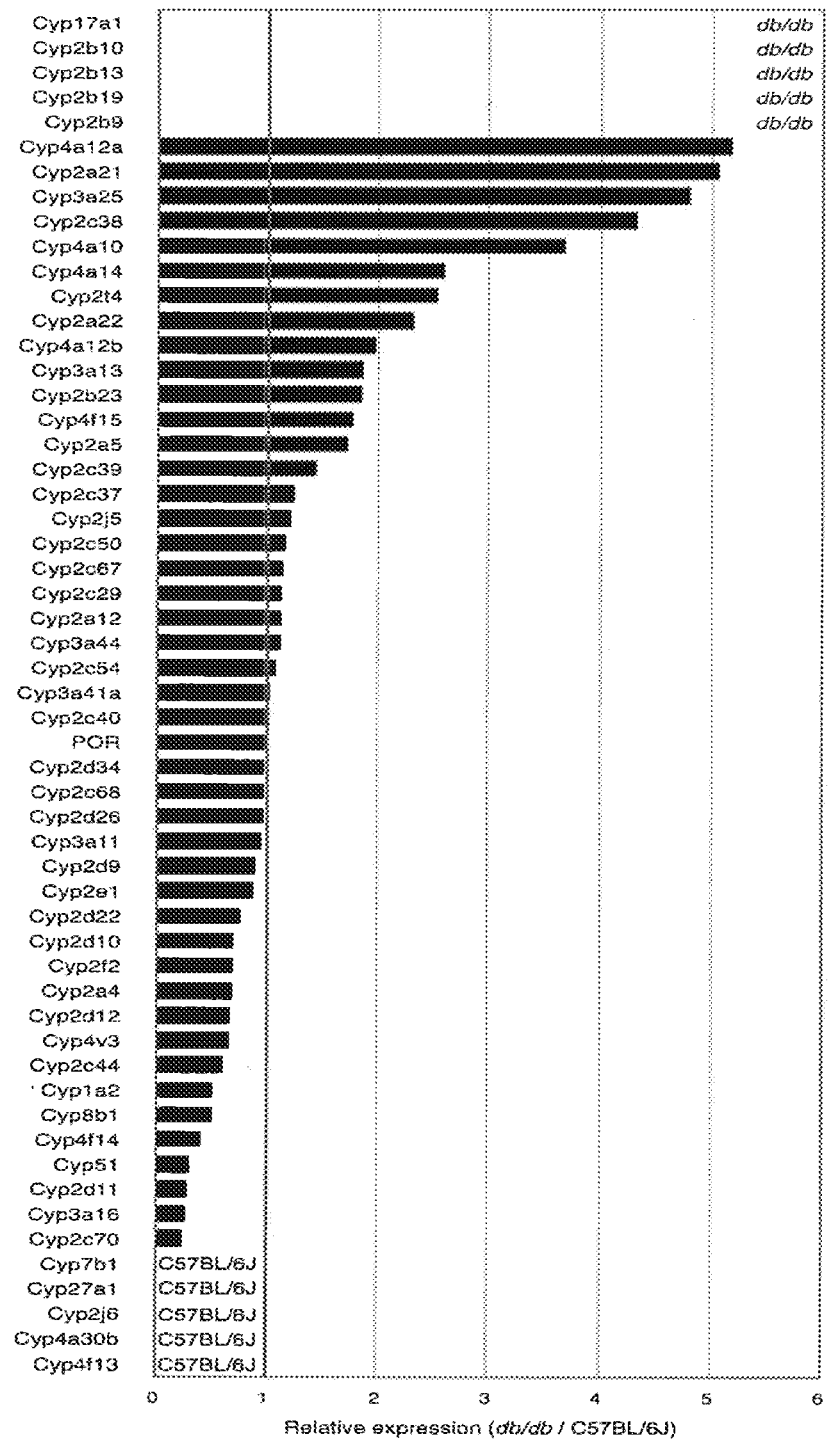
FIG. 2 shows the relative expression profile (db/db/C57BL/6J) of CYP450 proteins in C57BL/6J control and db/db mice. The proteins expressed exclusively in either C57BL/6J control or db/db mice are indicated with its corresponding mouse strain name.

Initially, the inventors attempted to identify all CYP proteins which are differently expressed in the normal and type 2 diabetic (T2DM) livers. To this end, liver tissues were collected from ten (10)-week-old C57BL/6J control and db/db mice which had developed obesity-induced T2DM. Membrane proteins were then isolated and identified by Fourier Transform Ion Cyclotron Resonance (FT-ICR) mass spectrometry (See FIG. 1). As a result, the inventors identified a total of fifty four (54) CYP proteins showing dynamic expression patterns in the normal and db/db mice livers (See FIG. 2). The inventors showed only the expression patterns of CYP2E1, CYP4A and POR, since CYP2E1 and CYP4A were shown to play a complementary role as a major microsomal catalyst of lipid peroxidases in fatty livers, while POR (NADPH cytochrome P450 reductase) is the only electron donor for all CYP450s.

Figure 6:
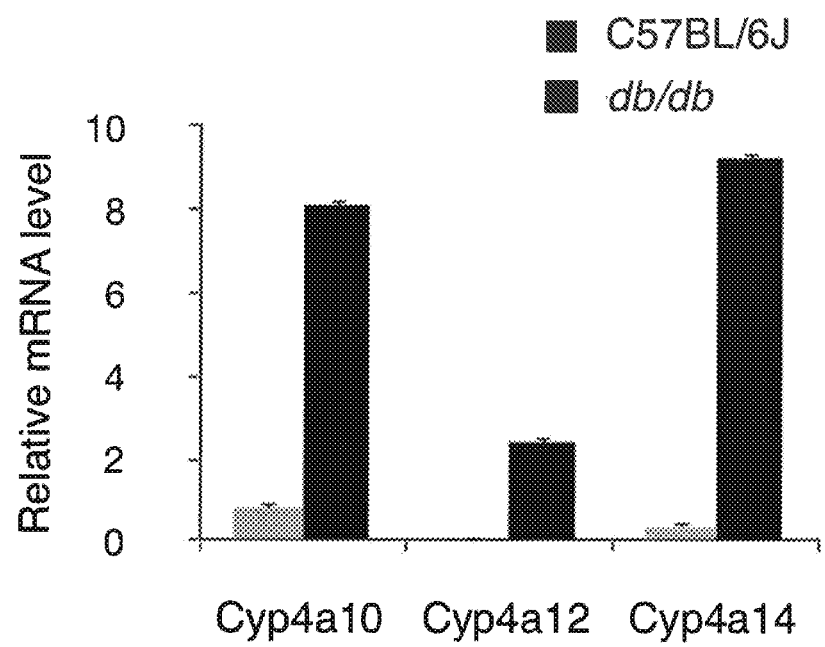
FIG. 6 shows the result of real-time RT-PCR of mouse Cyp4a mRNAs in the liver tissues of C57BL/6J control and db/db mice.
Figure 7:
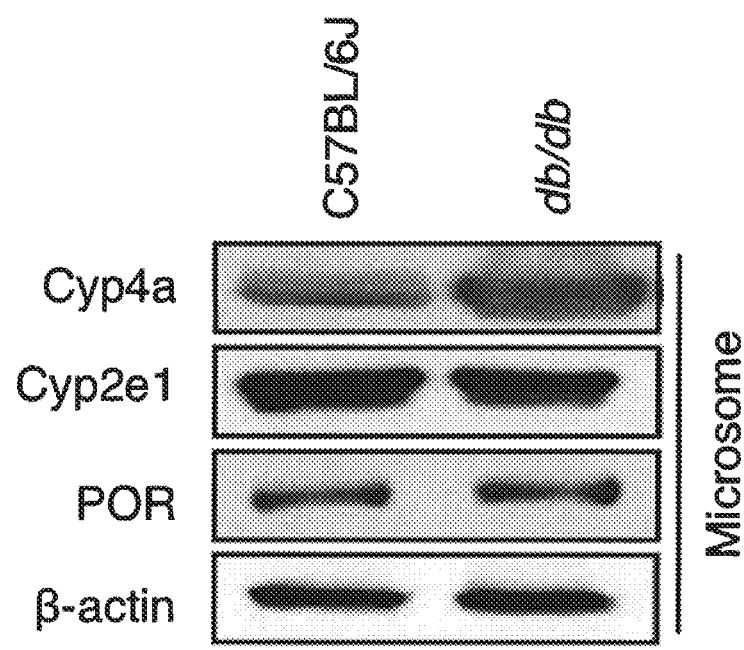
FIG. 7 shows the results of Western blotting assay of Cyp4a, Cyp2e1 and POR in the liver tissues of C57BL/6J control and db/db mice.
Figure 8:
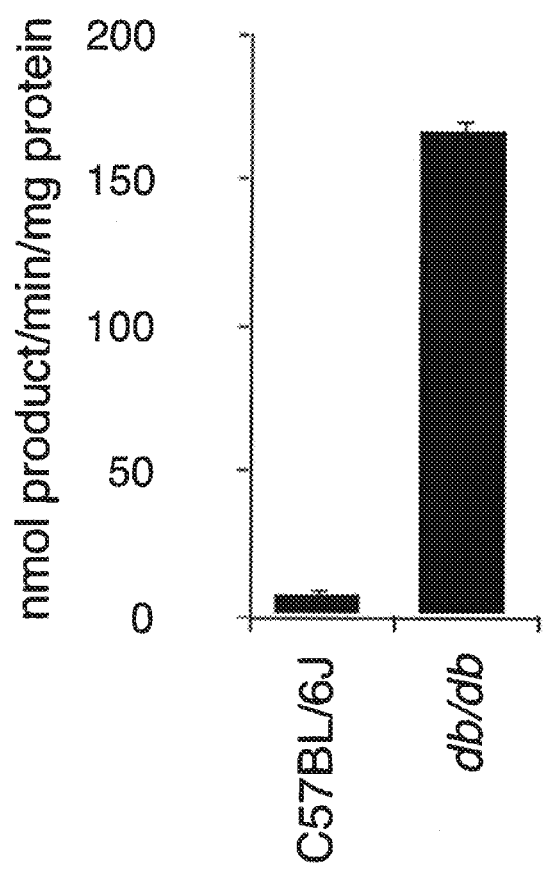

Interestingly, mouse Cyp4a isoforms, i.e. Cyp4a10, Cyp4a12 and Cyp4a14 were up-regulated in the db/db mice livers in comparison with the controls. However, the expression of Cyp2e1 was slightly decreased in the db/db mice livers, while that of POR in the db/db mice livers was similar to that of the controls (See FIG. 2). Real-time RT-PCR and Western Blot analysis were performed to verify the above proteomics results. As shown in mass spectrometry, the Cyp4a isoforms were highly expressed in the diabetic livers (See FIGS. 6 & 7), while the enzymatic activity of microsomal Cyp4a was also elevated (See FIG. 8). On the contrary, the expression of Cyp2e1 and POR was not up-regulated (See FIG. 7), demonstrating that CYP4A, not CYP2E1, acts as a major regulator in the development of hepatic T2DM.

Figure 5:
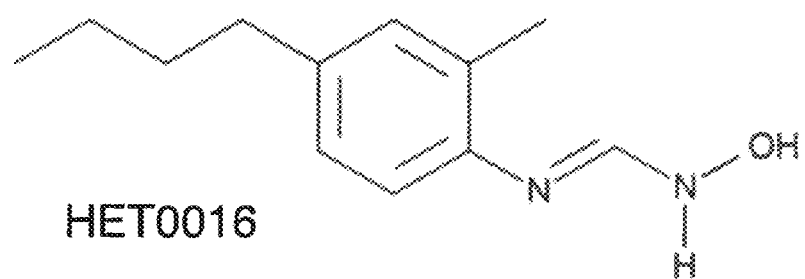
FIG. 5 illustrates a chemical structure of HET0016.
Figure 9:
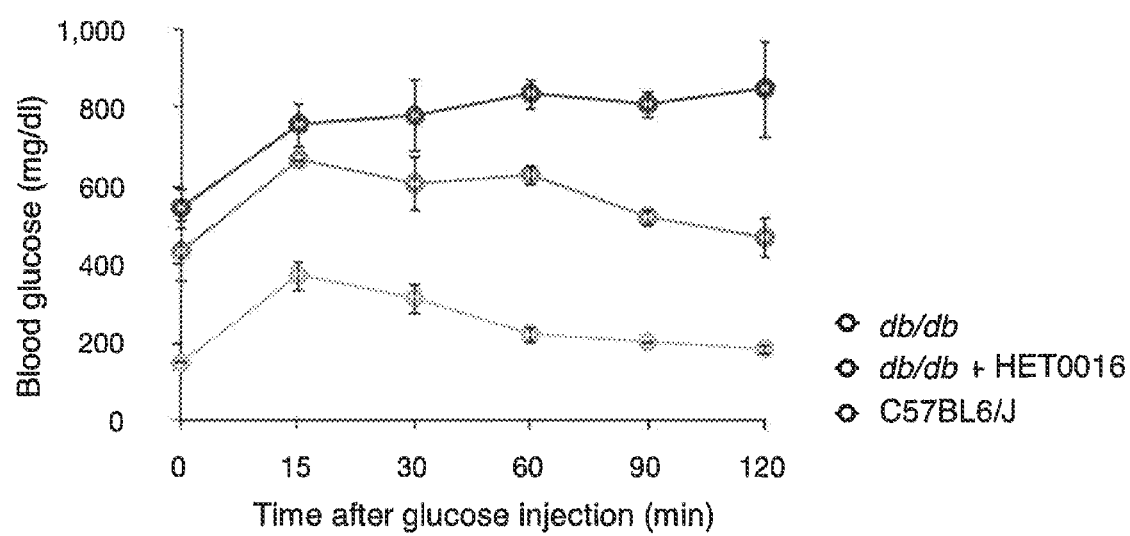
FIG. 9 shows the results of IPGTT in which 1 g/kg of glucose was injected intraperitoneally into C57BL/6J control and db/db mice, respectively, treated with 5 mg/kg/day of HET0016 or DMSO for 2 weeks, followed by measuring the level of blood glucose with a glucometer at the indicated time points. The obtained data are indicated as mean±SEM.
Figure 10:
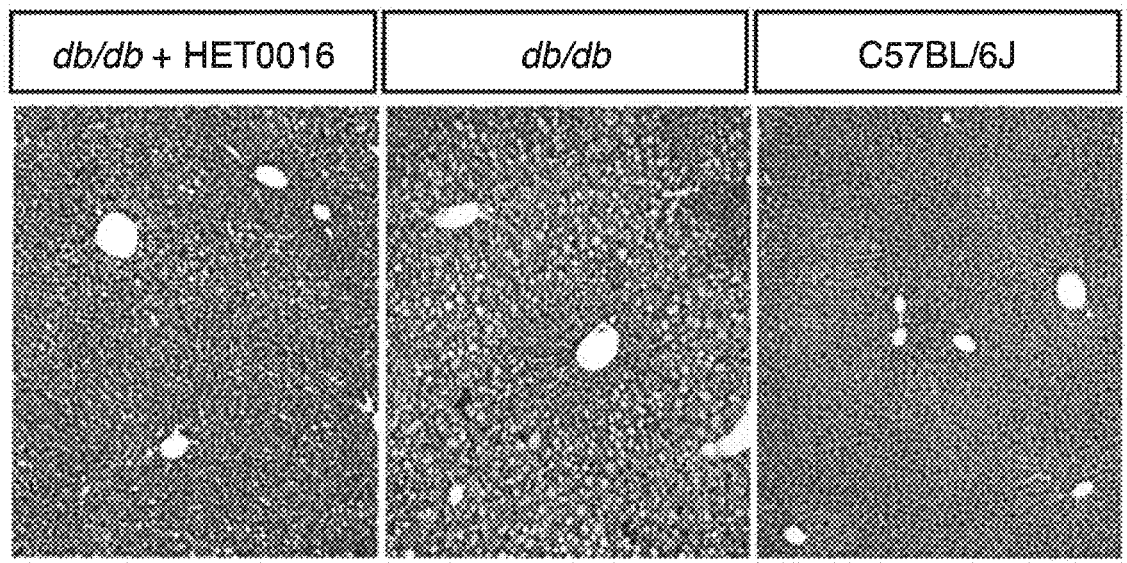
FIG. 10 shows the liver tissue sections of C57BL/6J control and db/db mice which were treated with HET0016 or DMSO, respectively, followed by hematoxylin-eosin staining.
Figure 11:
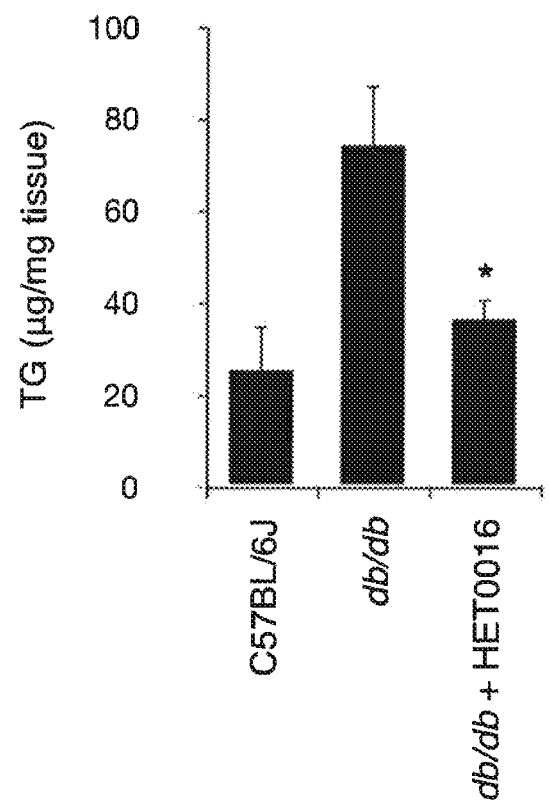
FIG. 11 shows the analysis of the MDA formation as an indicator of lipid peroxidation as measured by TBARS assay from the liver tissues of C57BL/6J control and db/db mice which were treated with HET0016 or DMSO, respectively. The obtained data are shown as mean±SEM. P values were determined by Student's t-test. *P<0.05 versus db/db control mice treated with DMSO.
Figure 13:
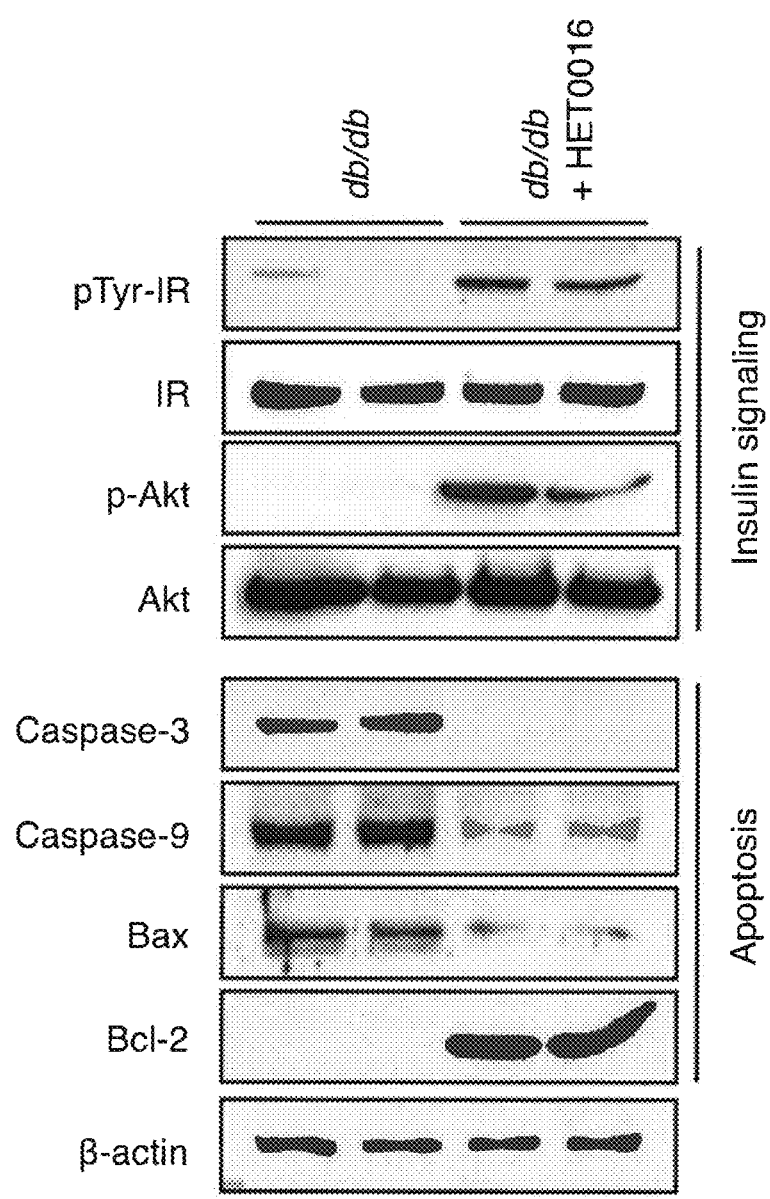
FIG. 13 shows the results of i) in vivo insulin signaling which was examined by investigating the phosphorylation of insulin receptor (IR) and Akt, and ii) apoptosis which was examined by investigating the expression of cleaved Caspase-3 and -9, Bax and Bcl-2 in the liver tissues of fasted db/db mice treated with either HET0016 or DMSO.
Figure 15:
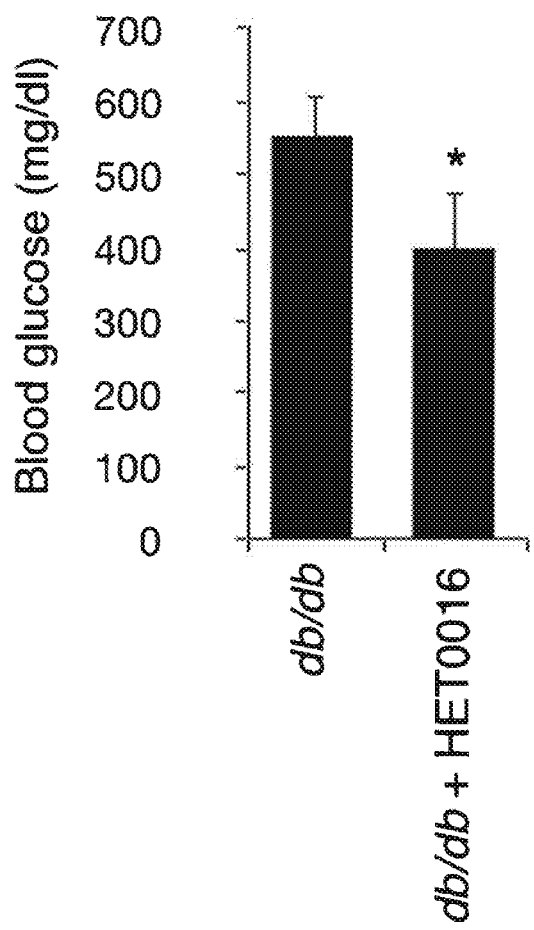
FIG. 15 shows the results of the level of blood glucose following 6 hours' fasting in the db/db mice and db/db mice treated with HET0016.
Figure 16:
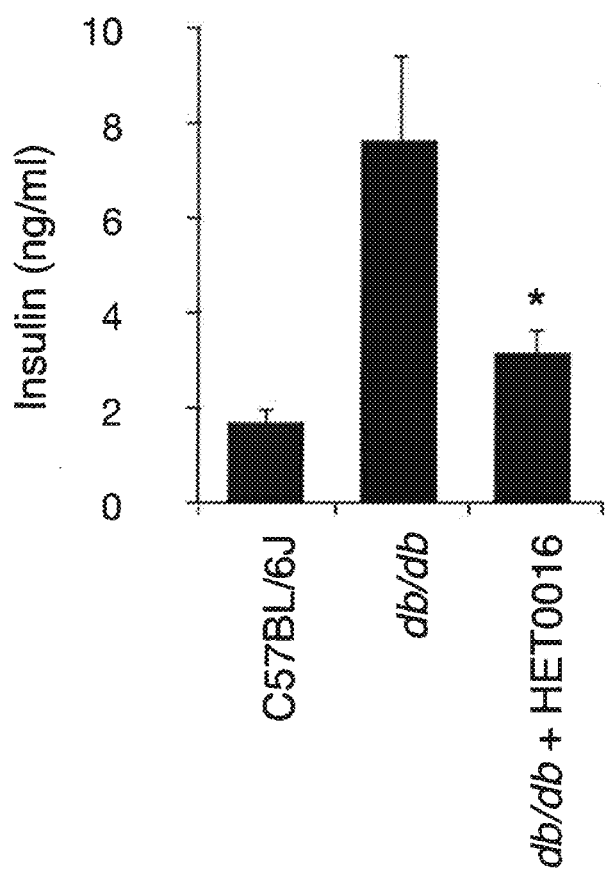
FIG. 16 shows the results of the level of insulin as measured by enzyme-linked immunosorbent assay (ELISA) on the serum which was obtained from C57BL/6J mice and db/db mice treated with HET0016 or DMSO

CYP4A is known to catalyze the ω-hydroxylation of fatty acids, especially lauric acid and arachidonic acid (AA) in mice. In order to study the role of CYP4A in diabetes, the inventors used a CYP4A-specific inhibitor, i.e. HET0016 (N-hydroxy-N'-(4-butyl-2-methylphenyl)-formamidine) which inhibits the enzymatic activity of those fatty acids (See FIG. 5). HET0016 was administered to eight (8)-week-old db/db mice through intraperitoneal injection for two (2) weeks (5 mg/kg/day). First, the inventors examined the effect of HET0016 on diabetic physiology. The intraperitoneal glucose tolerance test (IPGTT) showed that the inhibition of Cyp4a activity by using HET0016 significantly improved insulin resistance in diabetic mice (See FIG. 9). In addition, the level of blood glucose in diabetic mice was also decreased by HET0016 (See FIG. 15). The level of serum insulin in db/db mice, which was markedly higher than C57BL6J control mice, was notably reduced by the administration of HET0016 due to the decrease in insulin resistance (See FIG. 13). Further, severe hepatic steatosis in the db/db diabetic liver was relieved by HET0016 (See FIG. 10). The inventors further determined the relationship between CYP4A and hepatic lipid peroxidation which is involved with ER stress and elevated in T2DM patients. The inventors found that while hepatic lipid peroxidation was increased in the db/db mice in comparison with normal C57BL/6J mice, the increase of hepatic lipid peroxidation was notably reduced by the administration of HET0016 (See FIG. 11). The above results also strongly suggest that the hepatic inhibition of Cyp4a activity improves diabetic symptoms in the db/db mice.

Figure 3:
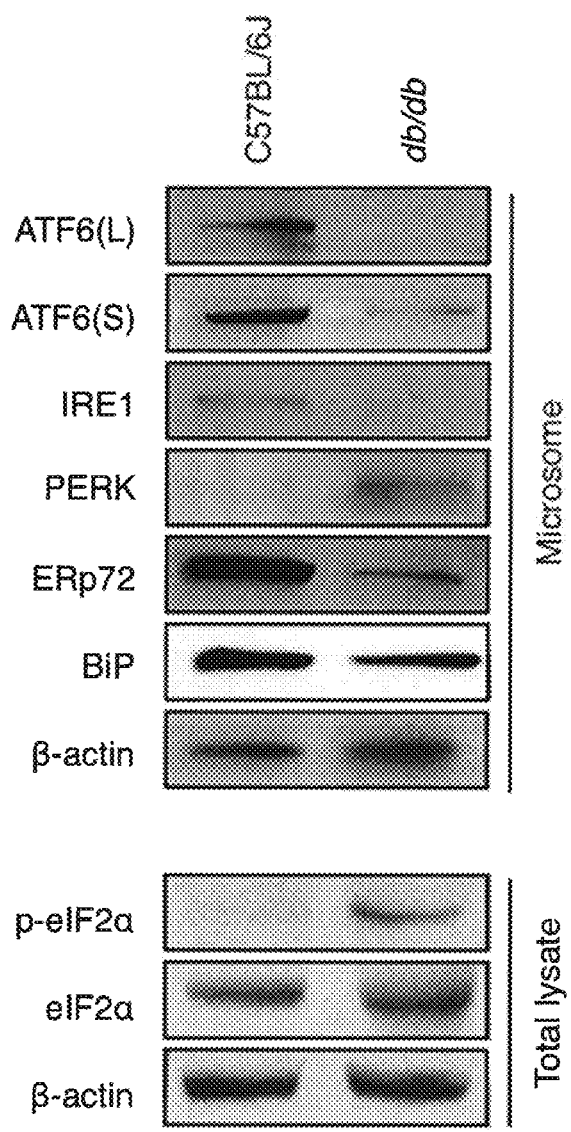
FIG. 3 shows the expression of ER stress markers and molecular chaperones by using Western blotting assay of the liver tissues of C57BL/6J control and db/db mice. ER-localized proteins (such as ATF6, IRE1, PERK, PRP72 and BiP) as isolated from microsomal fractions of the liver tissues were analyzed.
Figure 4:
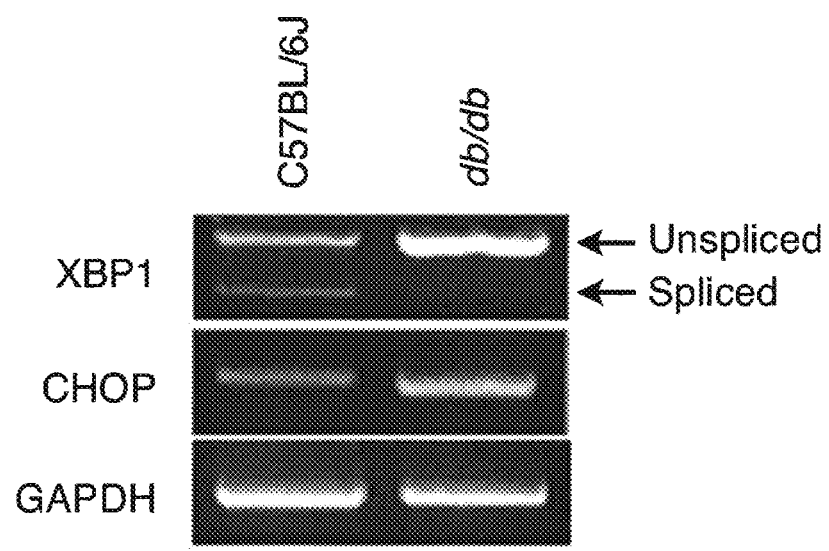
FIG. 4 determines the splicing of XBP1 and the transcription of CHOP in the liver tissues of C57BL/6J control and db/db mice via RT-PCR.
Figure 12:
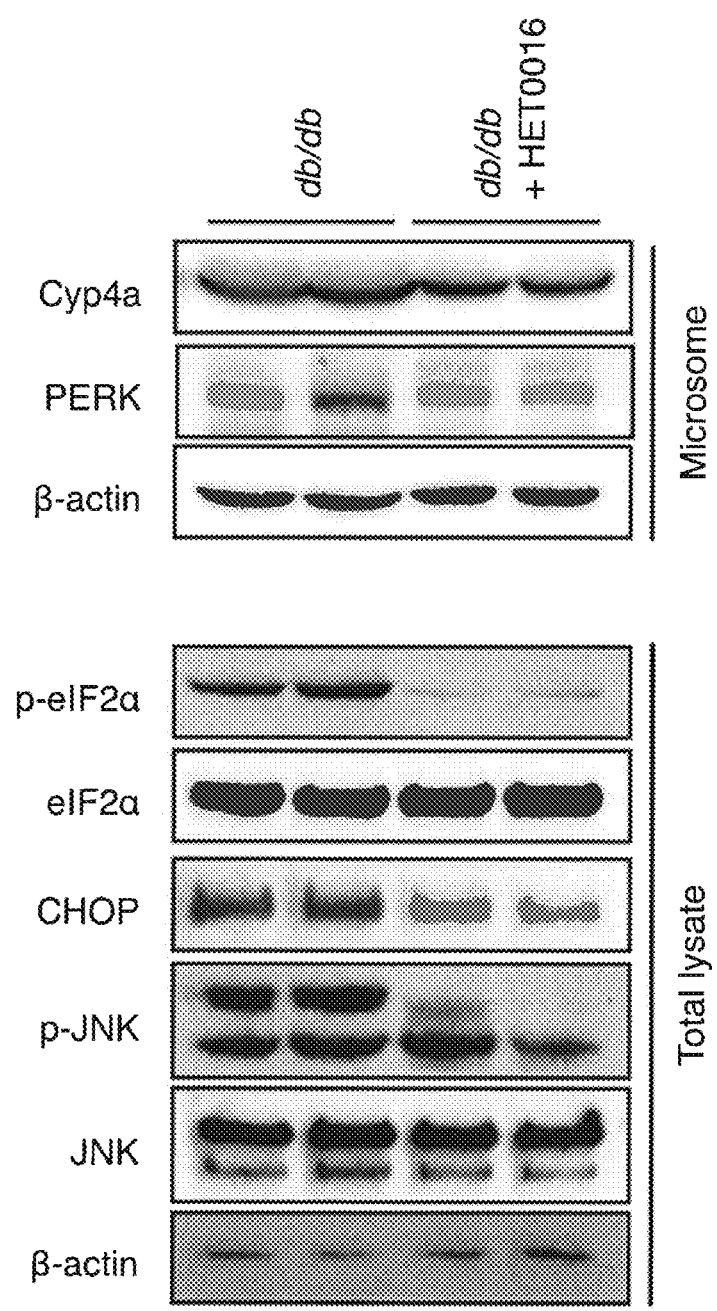
FIG. 12 shows the results of the expression of ER stress markers (such as PERK, phospho-eIF2α, CHOP and phospho-JNK) which was determined by Western blotting assay of the liver tissues obtained from fasted db/db mice treated with either HET0016 or DMSO. ER-localized proteins (such as Cyp4a and PERK) as obtained from the microsomal fraction of the liver tissues were analyzed. HET0016 was administered to 8-week-old db/db mice by intraperitoneal injection (5 mg/kg/day) for two (2) weeks.
Figure 14:
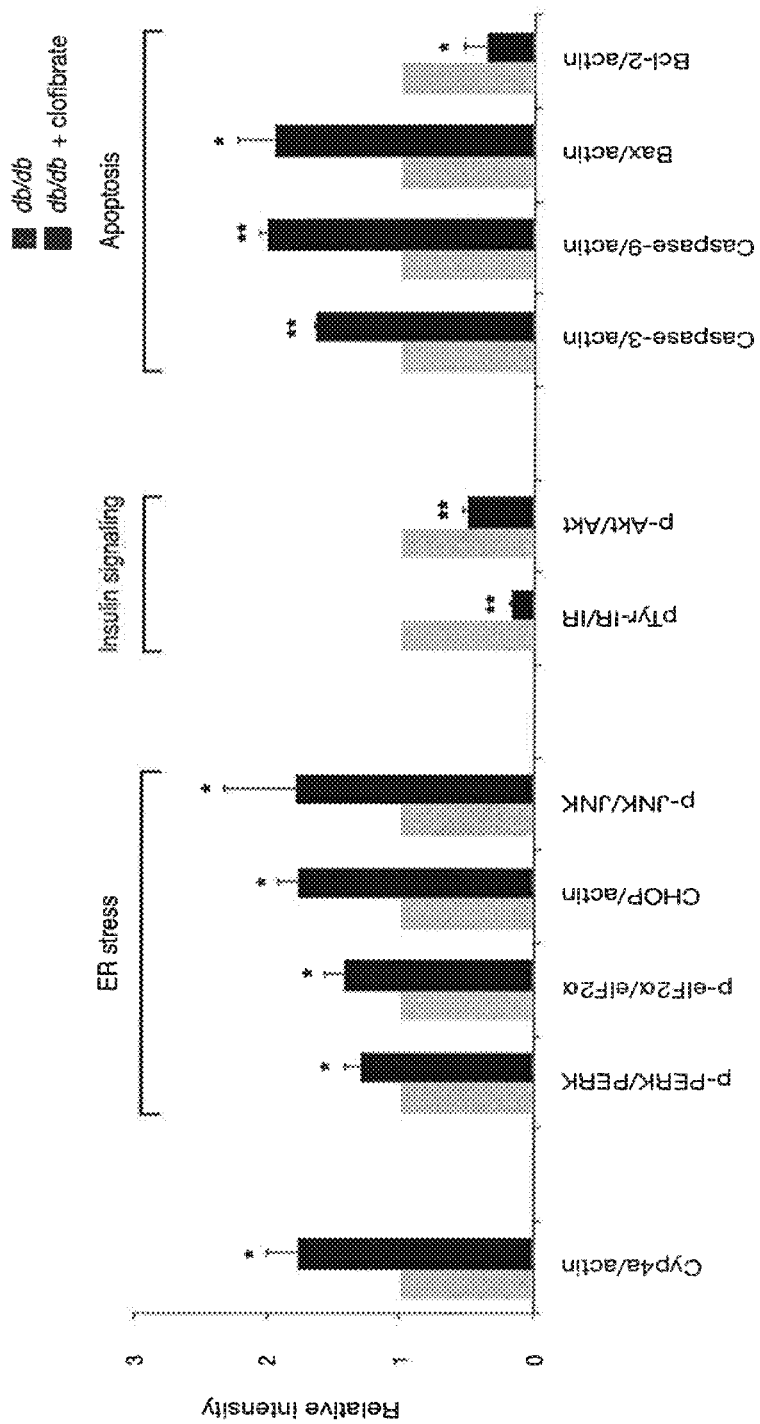
FIG. 14 shows the quantified results of ER stress, insulin signaling and apoptosis markers under the experimental conditions of FIGS. 12 & 13. Data are described as means±SEM. *P<0.05, **P<0.001 versus db/db control mice treated with DMSO.

Next, the inventors assessed whether the observed improvement of diabetic physiology in vivo by HET0016 was due to its effect on the regulation of ER stress which contributes to the development of obesity-induced diabetes. The UPR components play a dual role, i.e. acting as a beneficial regulator under physiological conditions or as a trigger of cellular dysfunction and apoptosis under the conditions of chronic stress. In a cell line system, the initial, combined activation of ATF6, IRE1 and PERK signaling generates a cyto-protective signal. In contrast, down-regulation of ATF6 and IRE1, coupled with the maintenance of PERK activation, induces apoptotic cell death. The inventors examined the expression of UPR components to see the status of UPR signaling in the diabetic liver, finding that the expression of ATF6 and IRE1 was reduced in the db/db mice livers (See FIG. 3) and that the splicing of XBP1 was suppressed in the db/db mice livers (See FIG. 4). The expression level of molecular chaperones, such as ERP72 and BiP was also reduced in the db/db mice. However, only PERK was up-regulated and its downstream signaling activity was enhanced in the diabetic liver (See FIG. 3), indicating that the livers of diabetic mice were in a severe apoptotic state caused by a prolonged ER stress. Intriguingly, it was found that the administration of the CYP4A inhibitor, i.e. HET0016 to the db/db mice reduced the expression of PERK and the activity of PERK downstream signaling (such as the phosphorylation status of eIF2α and the expression level of CHOP) (See FIGS. 12 & 14). Further, it was found that the activation of JNK, which is an important component of ER stress responses, was markedly decreased by HET0016, while the expression of Cyp4a was not changed by HET0016 (See FIGS. 12 & 14).

Recent reports demonstrated that ER stress-mediated JNK activation interferes with insulin activity and induces apoptosis in the liver. The findings in those reports prompted the inventors to investigate the effect of HET0016 on insulin resistance and apoptosis. The inventors found that the inhibition of Cyp4a activity with HET0016 in the db/db mice increased the phosphorylation of insulin receptor (IR) and Akt, meaning that insulin signaling was recovered in the diabetic liver by HET0016 treatment (See FIGS. 13 & 14). In addition, it was also found that the apoptosis of the diabetic liver tissues was inhibited by HET0016. Furthermore, the level of active forms of caspase-3 and -9 was also reduced and the expression of Bax, a pro-death protein, was suppressed, whereas the expression of Bcl-2, an anti-apoptotic regulator, was increased (See FIGS. 13 & 14). The above results strongly suggest that CYP4A is an important regulator of ER stress-induced insulin resistance and apoptosis in T2DM. As further finding supporting the above ideas, the inventors detected that inducing Cyp4a in the db/db mice with its specific inducer, clofibrate, caused the activation of PERK, eIF2α and JNK and the elevated expression of CHOP. Insulin resistance and apoptosis were also significantly regulated.

Figure 17:
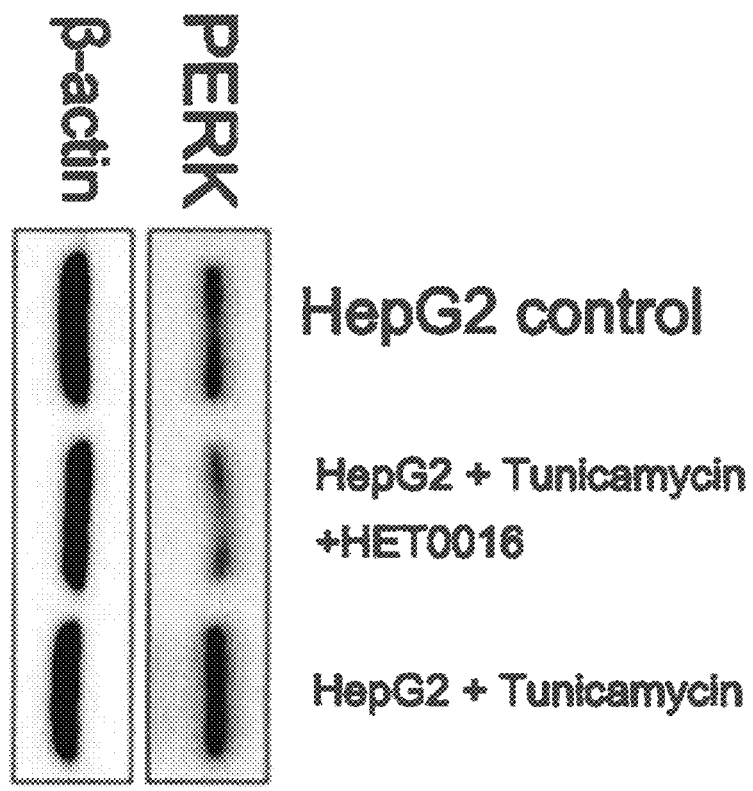
FIG. 17 shows the results after human hepatoma HepG2 cells were treated by 4 μg/ml of tunicamycin with or without 4 μM HET0016. The expression of PERK, an ER stress marker, was determined by Western blotting assay with the use of cell lysates and its primary antibodies.
Figure 18:
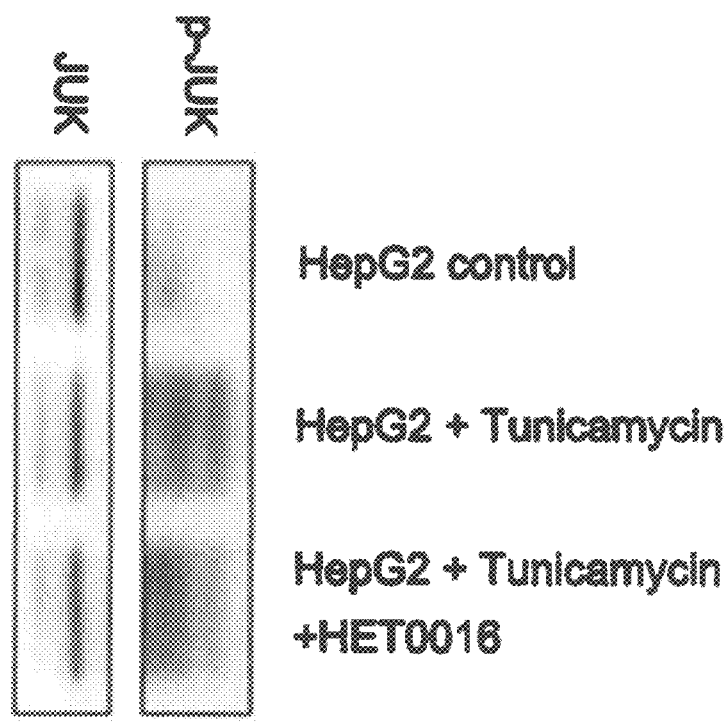
FIG. 18 shows the results after human hepatoma HepG2 cells were treated by 4 μg/ml of tunicamycin with or without 4 μM HET0016. The expression of p-JNK, an ER stress marker, was determined by Western blotting assay with the use of cell lysates and its primary antibodies.

Next, the inventors sought to determine whether the observed in vivo amelioration of ER stress by HET0016 was due to a direct cell-autonomous effect of HET0016 on ER stress or an indirect result of a complex in vivo interaction among diverse pathways. When ER stress was induced in human hepatoma HepG2 cells by 4 µg/ml of tumicamycin, the expression of PERK, phopho-eIF2α and phosphor-JNK was increased, respectively, as expected. Further, the combined treatment with 4 mM HET0016 was found to remarkably down-regulate the expression of all these three (3) ER stress markers in HepG2 cells (See FIGS. 17 & 18), suggesting that HET0016 directly reduces cellular ER stress.

Figure 19:
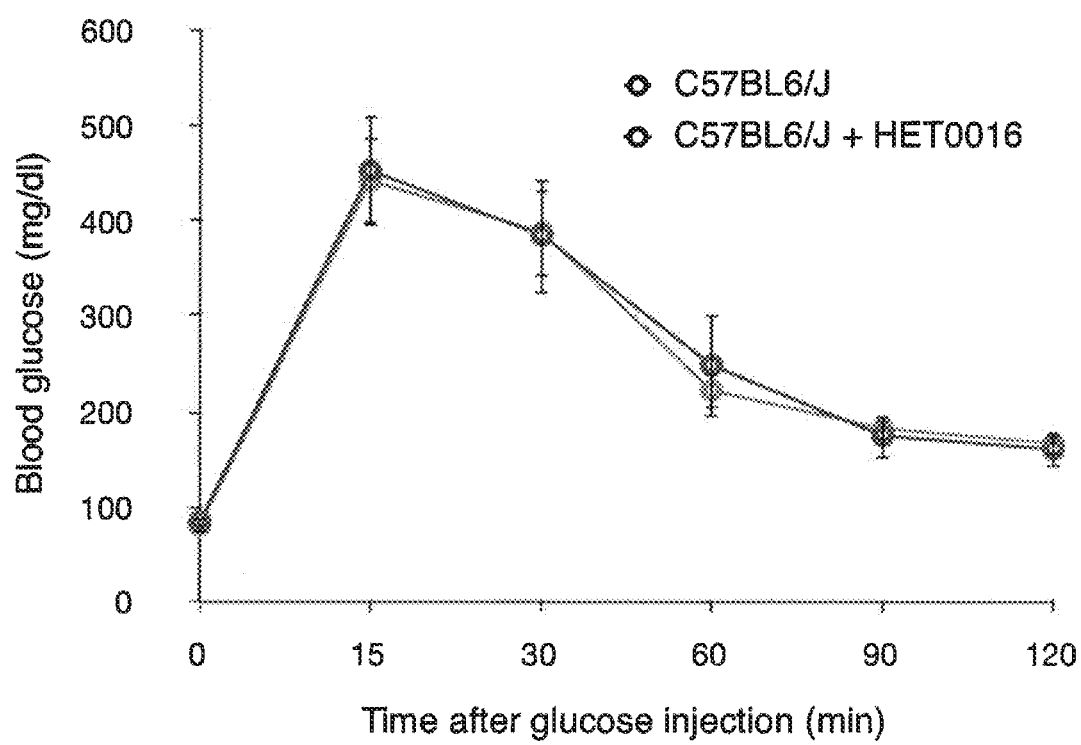
FIG. 19 shows the results of IPGTT (Intraperitoneal Glucose Tolerance Test) which was performed by injecting 1 g/kg of glucose intraperitoneally into C57BL/6J mice treated with 5 mg/kg/day of HET0016 or DMSO for two (2) weeks, followed by measuring the level of blood glucose with a glucometer at the indicated time points. The obtained data are shown as mean±SEM.
Figure 20:
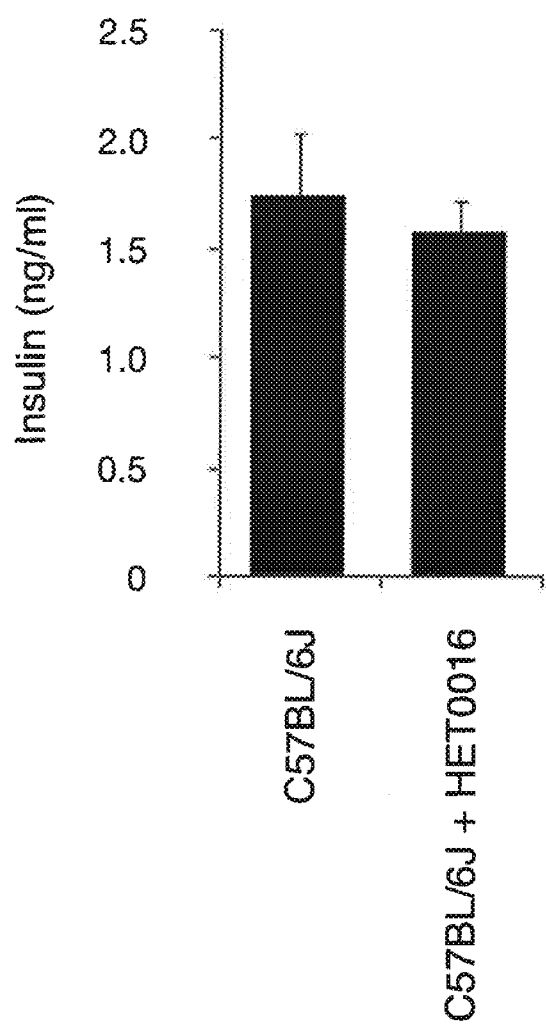
FIG. 20 shows the results of the level of insulin as measured by enzyme-linked immunosorbent assay (ELISA) on the serum which was obtained from C57BL/6J mice treated with HET0016 or DMSO.
Figure 21:
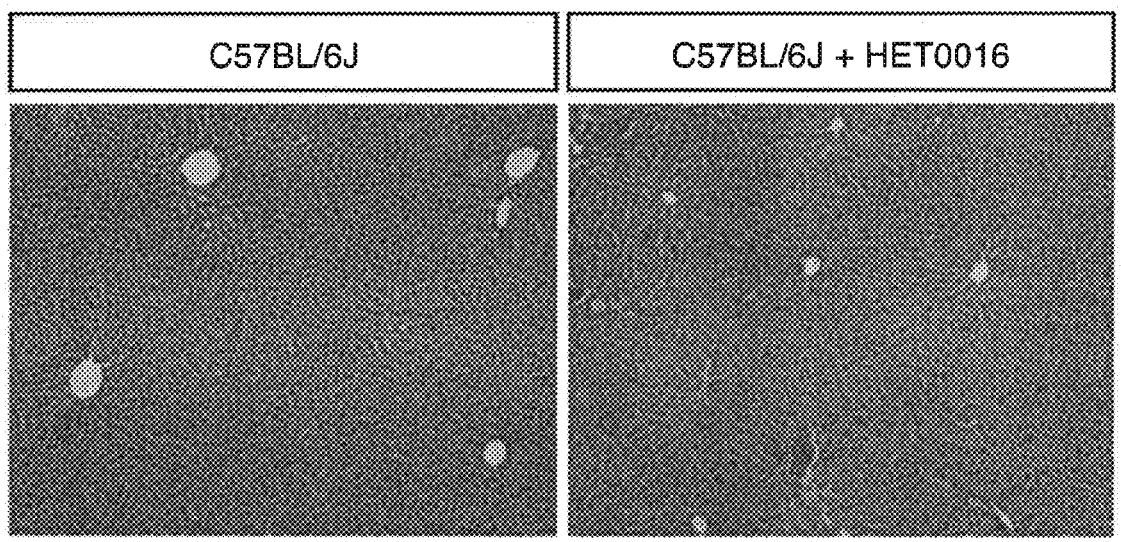
FIG. 21 shows the liver tissue sections of C57BL/6J control mice which were treated with HET0016 or DMSO, respectively, followed by hematoxylin-eosin staining.
Figure 22:
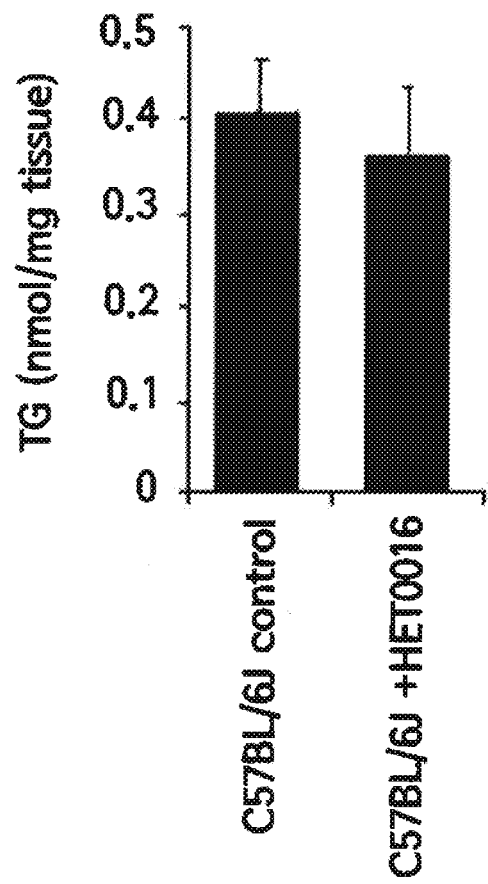
FIG. 22 shows the liver tissue sections of C57BL/6J control mice which were treated with HET0016 or DMSO, respectively, followed by measuring the level of TG.

One of the remaining questions was whether the inhibition of Cyp4a in normal mice could lead to any adverse effect which would be an obstacle to the use of CYP4A inhibition as a therapeutic option for the treatment of T2DM. For this purpose, eight (8) week-old male wild type C57BL/6J mice were injected intraperitoneally with the same doses of HET0016 as those which were injected into the db/db mice. The IPGTT results demonstrated that insulin resistance was not altered (See FIG. 19), while no differences were observed in serum insulin level (See FIG. 20), hepatic physiology (See FIG. 21) or hepatic steatosis (See FIG. 22).

In conclusion, the inventors demonstrated the physiological and functional importance of CYP4A in the development of T2DM by using the above mouse model. This is the first study to show a molecular mechanism by which CYP4A regulates ER stress-induced hepatic insulin resistance and apoptosis. In addition, the inventors' findings by using a CYP4A inhibitor, i.e. HET0016, provide new insights for the development of a novel therapeutic agent aimed at effectively reducing the activity of CYP4A which would decrease ER stress, enhance glucose tolerance, and reduce hepatic steatosis and apoptosis.

The invention claimed is:

1. A method for treating diabetes or fatty liver, comprising administering to a subject in need thereof an effective amount of a cytochrome P450 4A (CYP4A) inhibitor.

2. The method of claim 1, wherein the CYP4A inhibitor is any one selected from group consisting of N-hydroxy-N'-(4-butyl-2-methylphenyl)-formamidine, dibromododecenyl methylsulfonimide, 1-aminobenzotriazole, 17-octadecynoic acid, miconazole and derivatives thereof.

3. The method of claim 1, wherein diabetes is Type 2diabetes mellitus (T2DM).

4. The method of claim 1, wherein diabetes is induced by obesity.

5. The method of claim 1, wherein the CYP4A inhibitor inhibits endoplasmic reticulum (ER) stress.

6. The method of claim 1, wherein the CYP4A inhibitor decreases the level of blood insulin.

7. The method of claim 1, wherein the CYP4A inhibitor suppresses the apoptosis of Hepatocytes.

\* \* \* \* \*

SEQUENCE LISTING

<160> NUMBER OF SEQ ID NOS: 12

<210> SEQ ID NO 1
<211> LENGTH: 519
<212> TYPE: PRT
<213> ORGANISM: Homo sapiens

<400> SEQUENCE: 1

```
Met Ser Val Ser Val Leu Ser Pro Ser Arg Leu Leu Gly Asp Val Ser
1               5                   10                  15

Gly Ile Leu Gln Ala Ala Ser Leu Leu Ile Leu Leu Leu Leu Leu Ile
            20                  25                  30

Lys Ala Val Gln Leu Tyr Leu His Arg Gln Trp Leu Leu Lys Ala Leu
        35                  40                  45

Gln Gln Phe Pro Cys Pro Ser His Trp Leu Phe Gly His Ile Gln
    50                  55                  60

Glu Leu Gln Gln Asp Gln Glu Leu Gln Arg Ile Gln Lys Trp Val Glu
65                  70                  75                  80

Thr Phe Pro Ser Ala Cys Pro His Trp Leu Trp Gly Gly Lys Val Arg
                85                  90                  95

Val Gln Leu Tyr Asp Pro Asp Tyr Met Lys Val Ile Leu Gly Arg Ser
            100                 105                 110

Asp Pro Lys Ser His Gly Ser Tyr Arg Phe Leu Ala Pro Trp Ile Gly
```

```
            115                 120                 125
Tyr Gly Leu Leu Leu Asn Gly Gln Thr Trp Phe Gln His Arg Arg
    130                 135                 140

Met Leu Thr Pro Ala Phe His Tyr Asp Ile Leu Lys Pro Tyr Val Gly
145                 150                 155                 160

Leu Met Ala Asp Ser Val Arg Val Met Leu Asp Lys Trp Glu Glu Leu
                165                 170                 175

Leu Gly Gln Asp Ser Pro Leu Glu Val Phe Gln His Val Ser Leu Met
            180                 185                 190

Thr Leu Asp Thr Ile Met Lys Cys Ala Phe Ser His Gln Gly Ser Ile
        195                 200                 205

Gln Val Asp Arg Asn Ser Gln Ser Tyr Ile Gln Ala Ile Ser Asp Leu
    210                 215                 220

Asn Asn Leu Val Phe Ser Arg Val Arg Asn Ala Phe His Gln Asn Asp
225                 230                 235                 240

Thr Ile Tyr Ser Leu Thr Ser Ala Gly Arg Trp Thr His Arg Ala Cys
                245                 250                 255

Gln Leu Ala His Gln His Thr Asp Gln Val Ile Gln Leu Arg Lys Ala
            260                 265                 270

Gln Leu Gln Lys Glu Gly Glu Leu Glu Lys Ile Lys Arg Lys Arg His
        275                 280                 285

Leu Asp Phe Leu Asp Ile Leu Leu Leu Ala Lys Met Glu Asn Gly Ser
    290                 295                 300

Ile Leu Ser Asp Lys Asp Leu Arg Ala Glu Val Asp Thr Phe Met Phe
305                 310                 315                 320

Glu Gly His Asp Thr Thr Ala Ser Gly Ile Ser Trp Ile Leu Tyr Ala
                325                 330                 335

Leu Ala Thr His Pro Lys His Gln Glu Arg Cys Arg Glu Glu Ile His
            340                 345                 350

Ser Leu Leu Gly Asp Gly Ala Ser Ile Thr Trp Asn His Leu Asp Gln
        355                 360                 365

Met Pro Tyr Thr Thr Met Cys Ile Lys Glu Ala Leu Arg Leu Tyr Pro
    370                 375                 380

Pro Val Pro Gly Ile Gly Arg Glu Leu Ser Thr Pro Val Thr Phe Pro
385                 390                 395                 400

Asp Gly Arg Ser Leu Pro Lys Gly Ile Met Val Leu Leu Ser Ile Tyr
                405                 410                 415

Gly Leu His His Asn Pro Lys Val Trp Pro Asn Pro Glu Val Phe Asp
            420                 425                 430

Pro Phe Arg Phe Ala Pro Gly Ser Ala Gln His Ser His Ala Phe Leu
        435                 440                 445

Pro Phe Ser Gly Gly Ser Arg Asn Cys Ile Gly Lys Gln Phe Ala Met
    450                 455                 460

Asn Glu Leu Lys Val Ala Thr Ala Leu Thr Leu Leu Arg Phe Glu Leu
465                 470                 475                 480

Leu Pro Asp Pro Thr Arg Ile Pro Ile Pro Ile Ala Arg Leu Val Leu
                485                 490                 495

Lys Ser Lys Asn Gly Ile His Leu Arg Leu Arg Arg Leu Pro Asn Pro
            500                 505                 510

Cys Glu Asp Lys Asp Gln Leu
        515

<210> SEQ ID NO 2
```

```
<211> LENGTH: 519
<212> TYPE: PRT
<213> ORGANISM: Homo sapiens

<400> SEQUENCE: 2

Met Ser Val Ser Val Leu Ser Pro Ser Arg Arg Leu Gly Val Ser
1               5                   10                  15

Gly Ile Leu Gln Val Thr Ser Leu Leu Ile Leu Leu Leu Leu Ile
                20                  25                  30

Lys Ala Ala Gln Leu Tyr Leu His Arg Gln Trp Leu Leu Lys Ala Leu
                35                  40                  45

Gln Gln Phe Pro Cys Pro Pro Ser His Trp Leu Phe Gly His Ile Gln
50                      55                  60

Glu Phe Gln His Asp Gln Glu Leu Gln Arg Ile Gln Glu Arg Val Lys
65                  70                      75                  80

Thr Phe Pro Ser Ala Cys Pro Tyr Trp Ile Trp Gly Gly Lys Val Arg
                    85                  90                  95

Val Gln Leu Tyr Asp Pro Asp Tyr Met Lys Val Ile Leu Gly Arg Ser
                100                 105                 110

Asp Pro Lys Ser His Gly Ser Tyr Lys Phe Leu Ala Pro Arg Ile Gly
                115                 120                 125

Tyr Gly Leu Leu Leu Leu Asn Gly Gln Thr Trp Phe Gln His Arg Arg
130                     135                 140

Met Leu Thr Pro Ala Phe His Asn Asp Ile Leu Lys Pro Tyr Val Gly
145                 150                     155                 160

Leu Met Ala Asp Ser Val Arg Val Met Leu Asp Lys Trp Glu Glu Leu
                165                 170                 175

Leu Gly Gln Asp Ser Pro Leu Glu Val Phe Gln His Val Ser Leu Met
                180                 185                 190

Thr Leu Asp Thr Ile Met Lys Ser Ala Phe Ser His Gln Gly Ser Ile
                195                 200                 205

Gln Val Asp Arg Asn Ser Gln Ser Tyr Ile Gln Ala Ile Ser Asp Leu
                210                 215                 220

Asn Ser Leu Val Phe Cys Cys Met Arg Asn Ala Phe His Glu Asn Asp
225                     230                 235                 240

Thr Ile Tyr Ser Leu Thr Ser Ala Gly Arg Trp Thr His Arg Ala Cys
                    245                 250                 255

Gln Leu Ala His Gln His Thr Asp Gln Val Ile Gln Leu Arg Lys Ala
                260                 265                 270

Gln Leu Gln Lys Glu Gly Glu Leu Glu Lys Ile Lys Arg Lys Arg His
                275                 280                 285

Leu Asp Phe Leu Asp Ile Leu Leu Leu Ala Lys Met Glu Asn Gly Ser
                290                 295                 300

Ile Leu Ser Asp Lys Asp Leu Arg Ala Glu Val Asp Thr Phe Met Phe
305                 310                 315                 320

Glu Gly His Asp Thr Thr Ala Ser Gly Ile Ser Trp Ile Leu Tyr Ala
                    325                 330                 335

Leu Ala Thr His Pro Lys His Gln Glu Arg Cys Arg Glu Glu Ile His
                340                 345                 350

Gly Leu Leu Gly Asp Gly Ala Ser Ile Thr Trp Asn His Leu Asp Gln
                355                 360                 365

Met Pro Tyr Thr Thr Met Cys Ile Lys Glu Ala Leu Arg Leu Tyr Pro
                370                 375                 380

Pro Val Pro Gly Ile Gly Arg Glu Leu Ser Thr Pro Val Thr Phe Pro
```

```
                385                 390                 395                 400
Asp Gly Arg Ser Leu Pro Lys Gly Ile Met Val Leu Ser Ile Tyr
                    405                 410                 415

Gly Leu His His Asn Pro Lys Val Trp Pro Asn Leu Glu Val Phe Asp
                420                 425                 430

Pro Ser Arg Phe Ala Pro Gly Ser Ala Gln His Ser His Ala Phe Leu
                435                 440                 445

Pro Phe Ser Gly Gly Ser Arg Asn Cys Ile Gly Lys Gln Phe Ala Met
    450                 455                 460

Asn Gln Leu Lys Val Ala Arg Ala Leu Thr Leu Leu Arg Phe Glu Leu
465                 470                 475                 480

Leu Pro Asp Pro Thr Arg Ile Pro Ile Pro Met Ala Arg Leu Val Leu
                    485                 490                 495

Lys Ser Lys Asn Gly Ile His Leu Arg Leu Arg Arg Leu Pro Asn Pro
                500                 505                 510

Cys Glu Asp Lys Asp Gln Leu
        515

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
agccacaagg gcagtgttca gg                                                  22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ccaagcggcc attggaagaa ag                                                  22

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
gccttatacg gaaatatggc a                                                   21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tggaatcctg gccaacaatc                                                     20

<210> SEQ ID NO 7
<211> LENGTH: 28
<212> TYPE: DNA
<213> ORGANISM: Artificial Sequence
```

```
<220> FEATURE:
<223> OTHER INFORMATION: Primer

<400> SEQUENCE: 7
tgaattgctg ccagatccca ccaggatc                                          28

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
gttcagtggc tggtcaga                                                     18

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
aaacagagta gcagcgcaga ctgc                                              24

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
ggatctctaa aactagaggc ttggtg                                            26

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
catacaccac cacacctgaa ag                                                22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ccgtttccta gttcttcctt gc                                                22
```